(12) United States Patent
Shimosoyama et al.

(10) Patent No.: US 10,987,283 B2
(45) Date of Patent: Apr. 27, 2021

(54) DENTAL GLASS IONOMER CEMENT COMPOSITION FOR LUTING EXCELLENT IN REMOVABILITY

(71) Applicant: SHOFU INC., Kyoto (JP)

(72) Inventors: Shun Shimosoyama, Kyoto (JP); Katsuya Kimoto, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/357,399

(22) Filed: Mar. 19, 2019

(65) Prior Publication Data

US 2019/0380919 A1 Dec. 19, 2019

(30) Foreign Application Priority Data

Mar. 20, 2018 (JP) .............................. JP2018-052051
Mar. 15, 2019 (JP) .............................. JP2019-048085

(51) Int. Cl.
*A61K 6/889* (2020.01)
*A61K 6/77* (2020.01)

(52) U.S. Cl.
CPC ................ *A61K 6/889* (2020.01); *A61K 6/77* (2020.01)

(58) Field of Classification Search
None
See application file for complete search history.

(56) References Cited

U.S. PATENT DOCUMENTS

| | | | | | |
|---|---|---|---|---|---|
| 4,089,830 | A * | 5/1978 | Tezuka | .................. | A61K 6/889 523/116 |
| 4,360,605 | A * | 11/1982 | Schmitt | .................. | A61K 6/889 523/116 |
| 4,738,722 | A * | 4/1988 | Ibsen | .................. | C03C 3/064 106/35 |
| 4,775,592 | A * | 10/1988 | Akahane | .................. | C03C 17/22 428/406 |
| 4,900,697 | A * | 2/1990 | Akahane | .................. | A61K 6/889 501/57 |
| 5,063,257 | A * | 11/1991 | Akahane | .................. | A61K 6/77 523/116 |
| 5,151,453 | A * | 9/1992 | Ibsen | .................. | A61K 6/889 522/14 |
| 5,520,725 | A * | 5/1996 | Kato | .................. | A61K 6/30 106/35 |
| 5,844,019 | A * | 12/1998 | Kato | .................. | A61K 6/66 523/116 |
| 5,962,550 | A * | 10/1999 | Akahane | .................. | A61K 6/20 523/116 |
| 6,136,737 | A * | 10/2000 | Todo | .................. | A61K 6/30 501/73 |
| 6,214,101 | B1 * | 4/2001 | Nakaseko | .................. | A61K 6/20 106/35 |
| 6,264,472 | B1 * | 7/2001 | Okada | .................. | A61K 6/30 433/228.1 |
| 6,756,421 | B1 * | 6/2004 | Todo | .................. | A61K 6/30 523/116 |
| 6,872,244 | B2 * | 3/2005 | Kobayashi | .................. | A61L 24/12 106/35 |
| 7,041,714 | B2 * | 5/2006 | Takeshita | .................. | A61K 6/77 523/118 |
| 2003/0136303 | A1 * | 7/2003 | Kobayashi | .................. | A61K 6/889 106/35 |
| 2007/0072957 | A1 * | 3/2007 | Noguchi | .................. | A61K 6/20 523/116 |
| 2007/0254998 | A1 * | 11/2007 | Orlowski | .................. | C08L 33/14 524/425 |
| 2012/0077901 | A1 * | 3/2012 | Tanaka | .................. | A61K 6/889 523/116 |
| 2013/0266915 | A1 * | 10/2013 | Tsuruta | .................. | A61K 6/20 433/226 |
| 2014/0053758 | A1 * | 2/2014 | Nicholson | .................. | A61K 6/889 106/810 |
| 2015/0367023 | A1 * | 12/2015 | Miller | .................. | A61L 24/12 428/402 |
| 2016/0152795 | A1 * | 6/2016 | Lee | .................. | C08K 3/40 523/116 |

(Continued)

FOREIGN PATENT DOCUMENTS

| | | |
|---|---|---|
| EP | 0 510 211 | 10/1992 |
| EP | 0 836 468 | 4/1998 |
| JP | 4-173713 | 6/1992 |
| JP | 6-27049 | 4/1994 |
| JP | 7-53645 | 6/1995 |

(Continued)

OTHER PUBLICATIONS

Extended European Search Report dated Oct. 14, 2019, in corresponding European Application No. 19163849.3.

*Primary Examiner* — Peter A Salamon
(74) *Attorney, Agent, or Firm* — Wenderoth, Lind & Ponack, L.L.P.

(57) ABSTRACT

To provide a glass ionomer cement having excellent removality of the excess cement after setting because of having shape retaining property where a kneaded material does not drip and flow by their own weights, few risk of water sensitivity and excellent operability at the bonding such that excess cement can be removed easily after an application in an oral cavity in an early timing in spite of exhibiting a thin film thickness at the bonding. A dental glass ionomer cement composition for luting comprises at least; a component (a) acid reactive glass powder having an average particle diameter within a range of 4.5 to 7.0 μm, a component (b) polymer of an acid group-containing polymerizable monomer having a weight average molecular weight within a range of 30000 to 100000, a component (c) chelating agent and a component (d) water, wherein a plastic flow distance of a kneaded material before setting is 2 mm or less, and a removal possible time of an excess cement is 2 minutes or less.

14 Claims, No Drawings

(56) References Cited

U.S. PATENT DOCUMENTS

2016/0324729 A1\* 11/2016 Hokii ................... A61K 6/76
2017/0007506 A1\* 1/2017 Hokii ................... A61K 6/889
2017/0231874 A1 8/2017 Sakamoto et al.

FOREIGN PATENT DOCUMENTS

| JP | 9-48702 | 2/1997 |
| JP | 2813906 | 8/1998 |
| JP | 3452379 | 7/2003 |

\* cited by examiner

DENTAL GLASS IONOMER CEMENT COMPOSITION FOR LUTING EXCELLENT IN REMOVABILITY

CROSS-REFERENCE TO RELATED APPLICATIONS

This application is based on and claims the benefit of priorities from Japanese Patent Application Serial No. 2018-052051 (filed on Mar. 20, 2018) and Japanese Patent Application Serial No. 2019-048085 (filed on Mar. 15, 2019), the contents of which are hereby incorporated by reference in their entirety.

BACKGROUND OF THE INVENTION

Field of the Invention

The present invention relates to a dental glass ionomer cement for luting which adheres or bonds a dental prosthesis device to a tooth.

Description of the Related Art

In a dental practice, cement materials such as a dental adhesive resin cement and a dental glass ionomer cement for luting have been used as a material which adheres or bonds a dental prosthesis device such as a crown, an inlay and a bridge to a tooth in which a form was partially lost by caries or breakages.

A dental adhesive resin cement generally includes a matrix resin consisting of several kinds of polymerizable monomers, various fillers such as glass fillers and a polymerization catalyst as a main component and has high mechanical strength and high bond strength. Therefore, a dental adhesive resin cement is one of the dental material which has been used widely in recent years. However, a lot of dental adhesive resin cements have no self adhesive property to tooth substances, and when these materials are used, it is necessary to use a primer for tooth substances simultaneously, therefore the operation is complicated. In addition, since moisture-proofing is important in applying a primer for tooth substances, a risk of an adhesive failure caused by the influence of water has been concerned in a clinical case where it is hard to achieve moisture-proofing. Furthermore, the protective effect of the second caries by sustained release of a fluoride ion is recognized in only some commercial products.

In contrast, a dental glass ionomer cement for luting generally includes polycarboxylic acid, water and acid reactive glass powder represented by fluoroaluminosilicate glass as a main component, and a dental glass ionomer cement for luting exhibits self adhesive property to tooth substances by action of the polycarboxylic acid in the components. Therefore, one of advantage of a dental glass ionomer cement for luting is that it is not necessary to use a primer for tooth substances simultaneously. In addition, it is available in a clinical case where it is hard to achieve moisture-proofing because of including water in the components. Furthermore, because a fluoride ion is sustained release, the protective effect of the second caries can be expected.

In order to avoid lifting a dental prosthesis device in adhering or bonding a dental prosthesis device to a tooth and worsening the fitting, a kneaded material has been designed to have low viscosity so that a film thickness in these cement materials becomes thin. However, when the viscosity of a kneaded material is low, since extra cement overflowing from the clearance between teeth, that is excess cement, drips and flows by their own weights, various problems have been caused in clinical. Specifically, dripping and flowing of the excess cement on a soft tissue and contacting of the excess cement with a tongue cause not only a problem that an unpleasant feeling is imparted to patient but also a problem that a removal work after setting becomes complicated due to the widely spread excess cement. When the excess cement flows into under gingival margin, the removal in the details becomes more complicated, which becomes a factor of stress caused in both a dentist and a patient. In addition, because the kneaded material of the dental glass ionomer cement for luting has acidity, secretion of saliva is promoted by contacting of the dripped and flowed excess cement with a tongue of a patient, which leads water sensitivity of the cement. Such tendency is particularly remarkable in the infant that the secretion of saliva is active. The "water sensitivity" means a phenomenon that a poor setting is caused in a contact surface, which contacts with water during initial setting, of a glass ionomer cement.

In addition, another problem in the dental glass ionomer cement for luting is that a long time is required from attaching a dental prosthesis device in an oral cavity to removing the excess cement. A patient must wait in a state that the patient lightly bites an attached dental prosthesis device until the kneaded cement is initially set to some extent, and a dentist cannot remove the excess cement, therefore it is impossible to progress to the next work. This point also becomes a factor of stress caused in both a dentist and a patient.

From this kind of circumstance, a glass ionomer cement which has shape retaining property where a kneaded material does not drip and flow by their own weights, has excellent operability at the bonding such that excess cement can be removed easily after an application in an oral cavity in an early timing, and has few risk of water sensitivity in spite of exhibiting a thin film thickness at the bonding, has been required.

For the purpose of improving operability of a dental glass ionomer cement for luting, a technique shown below has been proposed until now.

Japanese Unexamined Patent Application Publication No. H4-173713 discloses a paste for dental glass ionomer cement containing glass powder, water-soluble polymer and water, and a kit for preparation of a dental glass ionomer cement consisting of the paste and polycarboxylic acid aqueous solutions are proposed. This document further discloses that, in this kit for preparation of a dental glass ionomer cement, a glass component, which was supplied in a form of powder conventionally, is supplied in a form of paste and therefore it is possible to measure accurately because a fixed amount discharge device is available, kneading with a polycarboxylic acid aqueous solution is very easily performed and is finished in a short time and therefore enough working time is provided, there are no disproportionation such as aggregation of powder by moisture absorption, and, a policlinic is always kept clean because glass is not scattered during work.

Japanese Examined Patent Application Publication No. H6-27049 discloses that excellent adhesive property and low collapse rate in an oral cavity are imparted to a dental cement and kneadability is remarkably improved by using aqueous dispersion liquid compounded with a polymer including carboxylic acid group, a graft copolymer including carboxylic acid group and polybasic acid in the specific ratio as dental cement setting liquid.

Japanese Examined Patent Application Publication No. H7-53645 discloses that dental cement setting liquid including a partially cross-linked watersoluble star-shaped polymer including a carboxylic acid group can simultaneously impart excellent kneadability and excellent durability such as crush resistance to a dental cement setting material.

Japanese Unexamined Patent Application Publication No. H9-48702 discloses a powder material containing a dental cement powder having an average particle diameter within a range of 0.01 to 20 μm and a sphericity (Fx) within a range of 0.50 to 0.95 and a dental cement composition consisting of the powder material and organic acid aqueous solution. This document further discloses that since the air between fine particles is removed immediately during the kneading with the organic acid aqueous solution by using the powder material including the dental cement powder, an uniform paste-form cement composition is provided easily to shorten a working time. In addition, this document discloses that the paste-form cement composition is insolubility to water, facilitates a restoration or a jointing work of a tooth and has high compressive strength and low collapse rate.

Japanese Patent Publication No. 2813906 discloses a dental cement setting agent consisting of a polymer-cement composite which is provided by polymerizing an unsaturated carboxylic acid monomer or by polymerizing a mixed monomer including the unsaturated carboxylic acid monomer and other copolymerizable unsaturated monomer in the water system medium in which a dental cement powder disperse. This document further discloses that this dental cement setting agent has more excellent operability and kneadability than a conventional setting agent on mixing with a dry cement powder content, and therefore a cement setting material which can be sufficiently kneaded in a short time without much skill and has excellent physical strength such as crush resistance and no unevenness is provided.

Japanese Patent Publication No. 3452379 discloses a preparation method of dental cement which comprises forming a dental cement composition including a fluoroaluminosilicate where an average particle diameter of the primary particle is 0.1 to 30 μm and SrO and $La_2O_3$ are contained in the specific ratio into a granular form having an average particle diameter within a range of about 100 to 1000 μm, filling in a container having an outlet of 1.0 to 4.0 mm in a diameter and quantifying by discharging the granular form dental cement composition from the outlet. This document further discloses that a cement setting material having excellent kneadability with setting agent aqueous solution and excellent handleability, exhibiting excellent X-ray contrast property without adding X-ray contrast media and having no unevenness in final properties is provided and a required amount of the dental cement composition can easily quantified by using this granular form dental cement composition.

However, these disclosed patent documents do not refer to a drip and removability after setting of the excess cement, a risk of water sensitivity and a improvement of time from applying in oral cavity to removing.

SUMMARY OF THE INVENTION

Technical Problem

In the conventional dental glass ionomer cement for luting, although the film thickness is thin, because the viscosity of a kneaded material is low, excess cement drips and flows by their own weights on attaching a dental prosthesis device. Therefore, an unpleasant feeling is imparted to patient and a removal work after setting becomes complicated due to the widely spread excess cement. Further, when the excess cement flows into under gingival margin, the removal in the details becomes more complicated, which becomes a factor of stress caused in both a dentist and a patient.

In addition, because the kneaded material has acidity, secretion of saliva is promoted by contacting of the dripped and flowed excess cement with a tongue of a patient, which leads water sensitivity of the cement. Further, there is another problem that a long time is required from attaching a dental prosthesis device in an oral cavity to removing the excess cement, a patient must wait in a state that the patient lightly bites an attached dental prosthesis device until the kneaded cement is initially set to some extent, and a dentist cannot remove the excess cement, therefore it is impossible to progress to the next work.

Solution to Problem

The present inventors have made intensive studies in order to solve the above problem, and as a result, have found that when a composition in which an average particle diameter of acid reactive glass powder and a weight average molecular weight of a polymer of an acid group-containing polymerizable monomer are adjusted within a specific range has a specific plastic flow distance, dripping of excess cement can be suppressed in spite of exhibiting thin film thickness on bonding. Furthermore, the present inventors have found that although excess cement easily drips and flows in accordance with the increase of the amount of the excess cement, dripping of the excess cement can be suppressed more effectively by imparting settable property which enables the removal of the excess cement in an early stage after attaching a dental prosthesis device in an oral cavity in addition to the above feature, even if there are much quantity of the excess cement. Based on such a knowledge, the present inventors have found that the dental glass ionomer cement composition for luting having the above features could solve simultaneously the problems which includes a drip of the excess cement, complexity of the removal after setting, a risk of water sensitivity and a long time required from attaching a dental prosthesis device in an oral cavity to removing the excess cement, leading to completion of the present invention.

The present invention provides a dental glass ionomer cement composition for luting comprising at least;

a component (a) acid reactive glass powder having an average particle diameter within a range of 4.5 to 7.0 μm, a component (b) polymer of an acid group-containing polymerizable monomer having a weight average molecular weight within a range of 30000 to 100000, a component (c) chelating agent and a component (d) water, wherein a plastic flow distance of a kneaded material before setting is 2 mm or less, and a removal possible time of an excess cement is 2 minutes or less.

In the dental glass ionomer cement composition for luting of the present invention, it is preferable that the plastic flow distance of the kneaded material before setting is 1 mm or less, and the removal possible time of the excess cement is 1 minute and 30 seconds or less.

It is preferable that the dental glass ionomer cement composition for luting of the present invention comprises;

30.0 to 75.0 wt. % of the component (a) acid reactive glass powder having an average particle diameter within a range of 4.5 to 7.0 μm, 5.0 to 30.0 wt. % of the component (b) polymer of an acid group-containing polymerizable monomer having a weight average molecular weight within a range of 30000 to 100000, 1.0 to 10.0 wt. % of the component (c) chelating agent, and 10.0 to 35.0 wt. % of the component (d) water.

In the dental glass ionomer cement composition for luting of the present invention, it is preferable that the average particle diameter of the component (a) acid reactive glass powder is within a range of 5.0 to 6.5 μm.

In the dental glass ionomer cement composition for luting of the present invention, it is preferable that the component (b) polymer of an acid group-containing polymerizable monomer is a polymer of an α-ß unsaturated carboxylic acid and the weight average molecular weight of the component (b) polymer of an acid group-containing polymerizable monomer is within a range of 50000 to 80000.

It is preferable that the component (c) chelating agent is tartaric acid.

In the dental glass ionomer cement composition for luting of the present invention, it is preferable that the component (b) polymer of an acid group-containing polymerizable monomer is a polymer of acrylic acid and 1-buten-1,2,4-tricarboxylic acid and/or a polymer of acrylic acid and 3-buten-1,2,3-tricarboxylic acid.

Advantageous Effects of Invention

The dental glass ionomer cement composition for luting of the present invention has shape retaining property where a kneaded material does not drip and flow by their own weights, in spite of exhibiting thin film thickness at the bonding and the excess cement can be removed easily after an application in an oral cavity in an early timing in the dental glass ionomer cement composition for luting of the present invention. Therefore, dripping of the excess cement can be suppressed regardless of an amount of the excess cement. Thus, a risk of water sensitivity can decrease, an unpleasant feeling of the patient by dripping and flowing of the excess cement on a soft tissue can be removed, operability on bonding is improved, for example, a removal work after setting becomes easy. In addition, it is not necessary to wait a long time from attaching a dental prosthesis device in an oral cavity to removing the excess cement, therefore, stress in the treatment for both a dentist and a patient can be reduced.

DETAILED DESCRIPTION OF THE PREFERRED EMBODIMENTS

Hereinafter, each components in the dental glass ionomer cement composition for luting of the present invention is described in detail.

It is necessary for a component (a) acid reactive glass powder of the present invention to include an acid reactive element such as metallic elements belongs to the group 1, the group 2 and the group 3 in the periodic table, and a fluorine element. Because the component (a) acid reactive glass powder includes an acid reactive element, the acid-base reaction of the component (a) acid reactive glass powder with the acid group contained in the component (b) polymer of an acid group-containing polymerizable monomer described later progresses in the presence of water.

Specific examples of an acid reactive element include sodium, potassium, calcium, strontium, barium, lanthanum, aluminum and zinc, but are not limited thereto. One or two or more kinds of these acid reactive element may be contained and a content thereof is not particularly limited. Further, it is preferable that the component (a) acid reactive glass powder includes an X-ray impermeable element in order to impart X-ray contrast property to the dental glass ionomer cement composition for luting of the present invention. Specific examples of an X-ray impermeable element include strontium, lanthanum, zirconium, titanium, yttrium, ytterbium, tantalum, tin, tellurium, tungsten and bismuth, but are not limited thereto. In addition, other element contained in the component (a) acid reactive glass powder is not particularly limited and the component (a) acid reactive glass powder in the present invention may include various elements.

Specific examples of the component (a) acid reactive glass powder include aluminosilicate glass, borosilicate glass, aluminoborate glass, boro aluminosilicate glass, phosphate glass, borate glass, silica glass wherein the above described acid reactive element, fluorine element and X-ray impermeable element are contained, but are not limited thereto.

Further, a particle shape of the component (a) acid reactive glass powder is not particularly limited, but arbitral particle shapes such as spherical, needle-like, plate-like, ground-like, and scaly-shape may be used without any limitation. These component (a) acid reactive glass powder may be used alone or in combination of two or more thereof.

A preparing process of the component (a) acid reactive glass powder is not particularly limited, but a component (a) acid reactive glass powder by any process such as a melting process, a vapor phase process and a sol-gel process may be used without any problem. Among them, the component (a) acid reactive glass powder prepared by a melting process or a sol-gel process which can easily control a kind of element contained in the acid-reactive element-containing glass powder and the content thereof is preferably used.

The component (a) acid reactive glass powder may be ground to use in order to obtain a desirable average particle diameter. A grinding method is not particularly limited, but an acid-reactive element-containing glass powder obtained by grinding which use any of wet or dry grinding methods may be used. Specifically the component (a) acid reactive glass powder may be ground by a high speed rotating mill such as a hammer mill and a turbo-mill, a container driving medium mill such as a ball mill and a vibration mill, a medium stirring mill such as a sand grinder and attritor, and a jet mill and the like.

An average particle diameter of the component (a) acid reactive glass powder must be within a range of 4.5 to 7.0 μm and is preferably within a range of 5.0 to 6.5 μm. In the present invention, the average particle diameter is calculated based on a grain size distribution on a volume basis measured by a laser diffraction grain size distribution measuring apparatus or the like. When the average particle diameter of the component (a) acid reactive glass powder is less than 4.5 μm, operability may decrease, for example mixing and kneading may become difficult and the viscosity of the kneaded material may become high. In addition, there is a risk that deterioration in mechanical strength may be caused because it becomes difficult to contain abundantly by increase of the surface area. Further, there is a case where the working time may become short. When the average particle diameter of the component (a) acid reactive glass powder is more than 7.0 μm, because the film thickness becomes thick, there is a case where a dental prosthesis device to be bonded may lift and therefore the fitting may decrease. In addition, there is a case where the excess cement drips and flows by their own weight because fluidity of the kneaded material becomes higher and that it is necessary to wait a long time to removing the excess cement because of sluggish setting.

The component (a) acid reactive glass powder may be treated with various surface treatments, heat treatment, aggregating treatment in a liquid phase or a vapor phase, microcapsulation in which particle is enclosed with an organic substance, grafting in which a surface is functionalized with an organic substance and the like to such a range that the acid-base reaction of the component (a) acid reactive glass powder with the acid group contained in the component (b) polymer of an acid group-containing polymerizable monomer described later is not influenced, in order to adjust operability setting characteristics, mechanical characteristics and the like of the dental glass ionomer cement composition for luting of the present invention. These treatments can be performed alone, or in a combination of a few kinds, with no problems. Among them, the surface treatment and heat treatment are preferable because it is easy to control various characteristics and those are superior in productivity.

Specific examples of the surface treating method of the component (a) acid reactive glass powder include washing with acid such as phosphoric acid or acetic acid, surface treatment with acidity compound such as tartaric acid or polycarboxylic acid, surface treatment with fluoride such as aluminum fluoride and surface treatment with silane compound such as γ-mercaptopropyl trimethoxy silane or tetramethoxy silane. The surface treating method which can be used in the present invention is not limited the above described method and these surface treating methods can be used alone, or in a combination thereof.

Specific examples of the heat treating method of the component (a) acid reactive glass powder include a treating method which includes heating for a range of 1 hour to 72 hours within a range of 100° C. to 800° C. using electric furnace. The heat treating method which can be used in the present invention is not limited the above described method and uni-processing or multi-stage processing can be used with respect to the treatment process.

The content of the component (a) acid reactive glass powder is preferably within a range of 30.0 to 75.0 wt. %, more preferably within a range of 45.0 to 75.0 wt. %, further preferably within a range of 45.0 to 70.0 wt. % based on the whole dental glass ionomer cement composition for luting. When the content of the component (a) acid reactive glass powder is less than 30.0 wt. %, fluidity of the kneaded material becomes higher and setting becomes sluggish and therefore there is a case where excess cement drips and flows by their own weight and there is a case where it is necessary to wait a long time to removing the excess cement. Further, there is a risk that mechanical strength may decrease. When the content of the component (a) acid reactive glass powder is more than 75.0 wt. %, operability may decrease, for example mixing and kneading may become difficult and the viscosity of the kneaded material may become high. Further, because the film thickness becomes thick, there is a case where a dental prosthesis device to be bonded may lift and therefore the fitting may decrease.

Any polymer can be used as the component (b) polymer of an acid group-containing polymerizable monomer as long as it is a polymer in which an acid group-containing polymerizable monomer having at least one or more an acid group in a molecule is polymerized without any limitation.

As the acidic group-containing polymerizable monomers which may be used for obtaining the component (b) polymer of an acid group-containing polymerizable monomer, any acidic group-containing polymerizable monomers may be used regardless of the type of acidic group. In addition, any acidic group-containing polymerizable monomers may be used regardless of the number or the type of radical polymerizable unsaturated groups (monofunctional groups or multifunctional groups) of the acidic group-containing polymerizable monomer. Specific examples of the acidic group of the acidic group-containing polymerizable monomer are not limited to, but include a phosphoryl group, a pyrophosphoryl group, a phosphonyl group, a carboxyl group, a sulfonyl group, and a thiophosphoryl group.

Specific examples of the unsaturated group of the acidic group-containing polymerizable monomer are not limited to, but include a (meth) acryloyl group, a styryl group, a vinyl group, and an aryl group. It is preferable that an acidic group-containing polymerizable monomer has a (meth) acryloyl group among these unsaturated groups.

Further, these acidic group-containing polymerizable monomers may contain together other functional group such as an alkyl group, halogen, an amino group, a glycidyl group, and a hydroxy group in a molecule.

Specific examples of an acidic group-containing polymerizable monomers which may be used for obtaining the component (b) polymer of an acid group-containing polymerizable monomer and has a (meth) acryloyl group as an unsaturated group, are specifically listed below.

Specific examples of an acidic group-containing polymerizable monomer which has a phosphoryl group are not limited to, but include (meth)acryloyloxymethyl dihydrogen phosphate, 2-(meth)acryloyloxyethyl dihydrogen phosphate, 3-(meth)acryloyloxypropyldihydrogenphosphate, 4-(meth)acryloyloxybutyldihydrogen phosphate, 5-(meth)acryloyloxypentyldihydrogenphosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis [2-(meth) acryloyloxyethyl]hydrogensphosphate, bis [3-(meth) acryloyloxypropyl] hydrogen phosphate, bis [4-(meth) acryloyloxybutyl] hydrogen phosphate, bis [6-(meta) acryloyloxyhexyl]hydrogen phosphate, bis [8-(meth) acryloyloxyoctyl] hydrogen phosphate, bis [9-(meth) acryloyloxynonyl] hydrogen phosphate, bis [10-(meth) acryloyloxydecyl] hydrogen phosphate, 1,3-di(meth) acryloyloxypropyl-2-dihydrogenphosphate, 2-(meth) acryloyloxyethylphenyl hydrogen phosphate, and 2-(meth) acryloyloxyethyl-2'-bromoethyl hydrogen phosphate.

Specific examples of an acidic group-containing polymerizable monomer which has a pyrophosphoryl group are not limited to, but include, bis [2-(meth) acryloyloxyethyl] pyrophosphate, bis [3-(meth) acryloyloxypropyl] pyrophosphate, bis [4-(meth) acryloyloxybutyl] pyrophosphate, bis [5-(meth) acryloyloxypentyl]pyrophosphate, bis [6-(meth) acryloyloxyhexyl] pyrophosphate, bis [7-(meth) acryloyloxyheptyl] pyrophosphate, bis [8-(meth) acryloyloxyoctyl] pyrophosphate, bis [9-(meth) acryloyloxynonyl] pyrophosphate, bis [10-(meth) acryloyloxydecyl]pyrophosphate, bis [12-(meth) acryloyloxydodecyl] pyrophosphate, and tris [2-(meth) acryloyloxyethyl] pyrophosphate.

Specific examples of an acidic group-containing polymerizable monomer which has a phosphonyl group are not limited to, but include 5-(meth) acryloyloxypentyl-3-phosphonopropionate, 6-(meth) acryloyloxyhexyl-3-phosphonopropionate, 10-(meth) acryloyloxydecyl-3-phosphonopropionate, 6-(meth) acryloyloxyhexyl-3-phosphonoacetate, and 10-(meth) acryloyloxydecyl-3-phosphonoacetate.

Specific examples of an acidic group-containing polymerizable monomer which has a carboxyl group are not limited to, but include (meth) acrylic acid, 2-chloro acrylic acid, 3-chloro(meth)acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth) acryloyloxyethylpyromellitic acid, 6-(meth) acryloyloxynaphthalene-1,2,6-tricarboxylic acid, 1-buten-1,2,4-tricarboxylic acid, 3-buten-1,2,3-tricarboxylic acid, N-(meth) acryloyl-p-aminobenzoic acid, N-(meth) acryloyl-5-aminosalicylic acid, 4-(meth) acryloyloxyethyltrimellitic acid and anhydride thereof, 4-(meth) acryloyloxybutyltrimellitic acid and anhydride thereof, 2-(meth) acryloyloxybenzoic acid, ß-(meth) acryloyloxyethyl hydrogen succinate, ß-(meth) acryloyloxyethyl hydrogen maleate, 11-(meth) acryloyloxy-1,1-undecanedicarboxylic acid, p-vinylbenzoic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid and anhydride thereof, 5-(meth) acryloylaminopentylcarboxylic acid, 6-(meth) acryloyloxy-1,1-hexanedicarboxylic acid, 8-(meth) acryloyloxy-1,1-octanedicarboxylic acid, 10-(meth) acryloyloxy-1,1-decanedicarboxylic acid, and 11-(meth) acryloyloxy-1,1-undecanedicarboxylic acid.

Specific examples of an acidic group-containing polymerizable monomer which has a sulfonate group are not limited to, but include 2-(meth) acrylamido-2-methylpropanesulfonic acid, styrenesulfonic acid, 2-sulfoethyl (meth) acrylate, 4-(meth) acryloyloxy benzenesulfonic acid, and 3-(meth) acryloyloxy propanesulfonic acid.

Specific examples of an acidic group-containing polymerizable monomer which has a thiophosphoryl group are not limited to, but include, 2-(meth) acryloyloxyethyl dihydrogendithiophosphate, 3-(meth) acryloyloxypropyl dihydrogendithiophosphate, 4-(meth) acryloyloxybutyl dihydrogendithiophosphate, 5-(meth) acryloyloxypentyl dihydrogendithiophosphate, 6-(meth) acryloyloxyhexyl dihydrogendithiophosphate, 7-(meth) acryloyloxyheptyl dihydrogendithiophosphate, 8-(meth) acryloyloxyoctyl dihydrogendithiophosphate, 9-(meth) acryloyloxynonyl dihydrogendithiophosphate, 10-(meth)acryloyloxydecyldihydrogendithiophosphate.

These acidic group-containing polymerizable monomers can be used not only singly but also in combinations of a plurality thereof for synthesize the component (b) polymer of an acid group-containing polymerizable monomer. Furthermore, the the component (b) polymer of an acid group-containing polymerizable monomer may be obtained by copolymerizing a polymerizable monomer containing one or more acidic group in a molecule and a polymerizable monomer containing no acidic group, without any problem.

It is preferable to use an α-ß unsaturated carboxylic acid based acidic group-containing polymerizable monomers among these acidic group-containing polymerizable monomers. The α-ß unsaturated carboxylic acid based acidic group-containing polymerizable monomer is not particularly limited and may be used regardless of the number of carboxylic groups in the molecule or the existence of a carboxylic anhydride group or other substituents.

Specific examples of an α-ß unsaturated carboxylic acid based acidic group-containing polymerizable monomer are not limited to, but include (meth) acrylic acid, 2-chloro acrylic acid, 3-chloro (meth) acrylic acid, 2-cyano acrylic acid, aconitic acid, mesaconic acid, maleic acid, maleic anhydride, itaconic acid, itaconic anhydride, fumaric acid, glutaconic acid, citraconic acid, utraconic acid, 1-buten-1,2,4-tricarboxylic acid, and 3-buten-1,2,3-tricarboxylic acid. Among these, it is more preferable that the component (b) polymer of an acid group-containing polymerizable monomer which is synthesized from only acrylic acid as a starting raw material or the component (b) polymer of an acid group-containing polymerizable monomer which is synthesized from two kinds as a starting raw material such as acrylic acid and maleic acid, acrylic acid and maleic anhydride, acrylic acid and itaconic acid, acrylic acid and 1-butene-1,2,4-tricarboxylic acid, and acrylic acid and 3-butene-1,2,3-tricarboxylic acid is used. From a point of view of exhibiting high shape retaining property, it is further preferable that the component (b) polymer of an acid group-containing polymerizable monomer which is synthesized from acrylic acid and an α-ß unsaturation carboxylic acid based acid group-containing polymerizable monomer in which the number of the carboxyl group per monomer unit is large such as acrylic acid and maleic acid, acrylic acid and maleic anhydride, acrylic acid and itaconic acid, acrylic acid and 1-butene-1,2,4-tricarboxylic acid, and acrylic acid and 3-butene-1,2,3-tricarboxylic acid is used. It is especially preferable that the component (b) polymer of an acid group-containing polymerizable monomer is a polymer of acrylic acid and 1-butene-1,2,4-tricarboxylic acid, and/or a polymer of acrylic acid and 3-butene-1,2,3-tricarboxylic acid is used.

The method of polymerizing various polymerizable monomers is not particularly limited, and a polymer polymerized by any methods such as solution polymerization, suspension polymerization, emulsion polymerization or the like, may be used without any limitation. In addition, a polymerization initiator and a chain transfer agent used at the time of synthesis of a polymer may be appropriately selected in order to obtain a desired polymer. The component (b) polymer of an acid group-containing polymerizable monomer obtained by such way can be used alone, or in a combination of a few kinds.

A weight average molecular weight of the component (b) polymer of an acid group-containing polymerizable monomer must be within a range of 30000 to 100000, and is preferable within a range of 50000 to 80000. Herein, the weight average molecular weight means the average molecular weight which is calculated based on molecular weight distribution measured by gel permeation chromatography. When the weight average molecular weight of the component (b) polymer of an acid group-containing polymerizable monomer is less than 30000, fluidity of the kneaded material becomes higher and setting becomes sluggish and therefore there is a case where the excess cement drips and flows by their own weight and there is a case where it is necessary to wait a long time to removing the excess cement. Further, there is a risk that mechanical strength may decrease. When the weight average molecular weight of the component (b) polymer of an acid group-containing polymerizable monomer is more than 100000, operability may decrease, for example mixing and kneading may become difficult and the viscosity of the kneaded material may become high. Further, because the film thickness becomes thick, a dental prosthesis device to be bonded may lift and therefore the fitting may decrease.

A polydispersity of the component (b) polymer of an acid group-containing polymerizable monomer is not particular limited, but is preferably 1.7 or more, and is more preferably 2.5 or more. When the polydispersity of the component (b) polymer of an acid group-containing polymerizable monomer is 1.7 or more, in dental glass ionomer cement composition for luting of the present invention, form maintenance property become higher and dripping and flowing by their own weights become hard. In addition, a time from attaching a dental prosthesis device in oral cavity to removing excess cement is shortened.

The content of the component (b) polymer of an acid group-containing polymerizable monomer is preferably within a range of 5.0 to 30.0 wt. %, more preferably within a range of 10.0 to 25.0 wt. % based on the whole dental glass ionomer cement composition for luting. When the content of the component (b) polymer of an acid group-containing polymerizable monomer is less than 5.0 wt. %, fluidity of the kneaded material becomes higher and setting becomes sluggish and therefore there is a case where the excess cement drips and flows by their own weight and there is a case where it is necessary to wait a long time to removing the excess cement. Further, there is a risk that mechanical strength may decrease. When the content of the component (b) polymer of an acid group-containing polymerizable monomer is more than 30.0 wt. %, operability may decrease, for example mixing and kneading may become difficult and the viscosity of the kneaded material may become high. Further, because the film thickness becomes thick, a dental prosthesis device to be bonded may lift and therefore the fitting may decrease.

Any chelating agent can be used as the component (c) chelating agent as long as it is coordinately bonded to a metal ion to form a chelate complex without any limitation.

Specific examples of the component (c) chelating agent include carboxylic acid compounds such as tartaric acid, citric acid, maleic acid, fumaric acid, malic acid, aconitic acid, tricarballylic acid, itaconic acid, salicylic acid, 1-butene-1,2,4-tricarboxylic acid, 3-butene-1,2,3-tricarboxylic acid, ethylenediamine tetraacetic acid, nitrilotriacetic acid, merit acid, trimellitic acid, pyromellitic acid and dihydroxybenzoic acid, phosphate compounds such as phosphoric acid, pyrophosphoric acid, tripoly phosphoric acid, and metal salt of basic acid thereof. The basic acid and metal salt thereof may be used alone or in combination of two or more thereof. Among them, it is preferable that tartaric acid is used as the component (c) chelating agent.

The content of the component (c) chelating agent is preferably within a range of 1.0 to 10.0 wt. %, more preferably within a range of 2.0 to 8.0 wt. %. based on the whole dental glass ionomer cement composition for luting. When the content of the component (c) chelating agent is less than 1.0 wt. %, there is a case where the working time may become short. When the content of the component (c) chelating agent is more than 10.0 wt. %, there is a risk that mechanical strength may decrease.

The component (d) water acts as functions as a solvent to dissolve the component (b) polymer of an acid group-containing polymerizable monomer and is an essential component for dispersing a metal ion eluted from the component (a) acid reactive glass powder to induce crosslinkage reaction with the component (b) polymer of an acid group-containing polymerizable monomer.

Any water can be used as the component (d) water as long as it does not contain impurities adversely affecting on the settability and mechanical strength of the dental glass ionomer cement composition for luting without any limitation. Specifically, it is preferably to use distilled water or ion-exchanged water.

The content of the component (d) water is preferably within a range of 10.0 to 35.0 wt. %, more preferably within a range of 10.0 to 25.0 wt. %, further preferably within a range of 15.0 to 25.0 wt. % based on the whole dental glass ionomer cement composition for luting. When the content of the component (d) water is less than 10.0 wt. %, because the content of the component (a) acid reactive glass powder and the component (b) polymer of an acid group-containing polymerizable monomer relatively increases, there is a case where operability may decrease, for example mixing and kneading may become difficult and the viscosity of the kneaded material may become high. In addition, there is a case where the working time may become short, and a dental prosthesis device to be bonded may lift and therefore the fitting may decrease. When the content of the component (d) water is more than 35.0 wt. %, fluidity of the kneaded material becomes higher and setting becomes sluggish and therefore there is a case where the excess cement drips and flows by their own weight and there is a case where it is necessary to wait a long time to removing the excess cement. Further, there is a risk that mechanical strength may decrease.

A plastic flow distance of the kneaded material before setting in the dental glass ionomer cement composition for luting of the present invention must be 2 mm or less and is preferably 1 mm or less, and is most preferably 0 mm. When the plastic flow distance is more than 2 mm, because the excess cement drips and flows and contacts with a tongue or a soft tissue, an unpleasant feeling is imparted to patient and operability is adversely affected because a removal work after setting becomes complicated. In addition, a risk of water sensitivity is led.

Herein, the plastic flow distance in the present invention means a distance in which a kneaded material drips and flows by their own weights when 0.3 g of the kneaded material is placed in a horizontal and smooth glass plane such that the diameter is within 10 mm and thereafter the glass plane is rotated to vertical to leave to stand until the kneaded material is set in environment of room temperature of 23±1° C. (that is, a distance from the position of the lowermost end of the kneaded material before the plastic flow to the position of the lowermost end of the kneaded material after setting).

The removal possible time of the excess cement of the dental glass ionomer cement composition for luting of the present invention must be 2 minutes or less and is preferably 1 minute and 30 seconds or less. When the removal possible time of the excess cement is more than 2 minutes, even if the plastic flow distance is 2 mm or less, there is a case where dripping of the excess cement is not suppressed effectively in the case that an amount of the excess cement is large. In addition, a patient must wait in a state that the patient lightly bites an attached dental prosthesis device and a dentist cannot remove the excess cement, therefore it is impossible to progress to the next work. Herein, the removal possible time of the excess cement in the present invention means a time, in the case in which when 0.3 g of the kneaded material is clamped between bottom surfaces of two rectangular resin blocks (12 mm of length×16 mm of width×10 mm of height) to strongly pressed by two resin blocks to protrude the kneaded material from the clearance in environment of room temperature of 23±1° C., and thereafter, it is placed into a thermostatic chamber of 37° C.—70% after 1 minute and 30 seconds from a start of kneading, from the placing into the thermostatic chamber to the timing where the kneaded material protruded from the clearance of the resin blocks can be removed in one lump.

Preferable ranges of the contents of each components which can exhibit the above described feature in the dental glass ionomer cement composition for luting of the present invention based on the whole composition are 30.0 to 75.0 wt. % of the component (a) acid reactive glass powder having an average particle diameter within a range of 4.5 to 7.0 μm, 5.0 to 30.0 wt. % of the component (b) polymer of an acid group-containing polymerizable monomer having a weight average molecular weight within a range of 30000 to 100000, 1.0 to 10.0 wt. % of the component (c) chelating agent, and 10.0 to 35.0 wt. % of the component (d) water.

In the dental glass ionomer cement composition for luting constituted in such content ranges, when the plastic flow distance of the kneaded material before setting is 2 mm or less and the removal possible time of the excess cement is 2 minutes or less, a glass ionomer cement which has shape retaining property where a kneaded material does not drip and flow by their own weights, has excellent operability at the bonding such that excess cement can be removed easily after an application in an oral cavity in an early timing, and has few risk of water sensitivity in spite of exhibiting a thin film thickness at the bonding, is provided.

More preferable ranges of the contents of each components based on the whole composition are 45.0 to 75.0 wt. % of the component (a) acid reactive glass powder having an average particle diameter within a range of 4.5 to 7.0 μm, 10.0 to 25.0 wt. % of the component (b) polymer of an acid group-containing polymerizable monomer having a weight average molecular weight within a range of 30000 to 100000, 1.0 to 10.0 wt. % of the component (c) chelating agent, and 10.0 to 25.0 wt. % of the component (d) water.

In the dental glass ionomer cement composition for luting constituted in such content ranges, when the plastic flow distance of the kneaded material before setting is 2 mm or less and the removal possible time of the excess cement is 2 minutes or less, the above described effects are remarkably exhibited and an excellent mechanical characteristic is exhibited.

Further preferable ranges of the contents of each components based on the whole composition are 45.0 to 70.0 wt. % of the component (a) acid reactive glass powder having an average particle diameter within a range of 4.5 to 7.0 μm, 10.0 to 25.0 wt. % of the component (b) polymer of an acid group-containing polymerizable monomer having a weight average molecular weight within a range of 30000 to 100000, 2.0 to 8.0 wt. % of the component (c) chelating agent, and 15.0 to 25.0 wt. % of the component (d) water.

In the dental glass ionomer cement composition for luting constituted in such content ranges, when the plastic flow distance of the kneaded material before setting is 2 mm or less and the removal possible time of the excess cement is 2 minutes or less, the above described effects are remarkably exhibited and an extremely excellent operability and mechanical characteristic are exhibited, and therefore an extremely preferable dental glass ionomer cement composition for luting is provided.

Further, a surfactant can be contained in the dental glass ionomer cement composition for luting of the present invention to such a range that various properties are not influenced, for the purpose of improving kneadability.

The surfactant which can be used in the dental glass ionomer cement composition for luting of the present invention may be any of an ionic surfactant and a nonionic surfactant.

Specific examples of the anionic surfactant in the ionic surfactant include aliphatic carboxylic acid metal salts such as sodium stearate, sulfated aliphatic carboxylic acid metal salts such as sodium dioctyl sulfosuccinate, and metal salts of higher alcohol sulfate ester such as sodium stearyl sulfate. In addition, examples of the cationic surfactant include an adduct of higher alkylamine and ethylene oxide, amines made from lower amine, and alkyltrimethylammonium salts such as lauryltrimethylammoniun chloride. Further, examples of the amphoteric surfactant include metal salts of higher alkylaminopropionic acid such as sodium stearylaminopropionate, and betaines such as lauryldimethylbetaine.

Examples of the nonionic surfactant include polyethylene glycol type and polypropylene glycol type in which ethylene oxide or propylene oxide is added to higher alcohols, alkyl phenols, fatty acids, higher fatty amines, or aliphatic amides, and polyhydric alcohol type in which polyhydric alcohols, diethanolamines, or saccharides is ester bonded to a fatty acid.

The aforementioned surfactants are not limited to these, but can be used without any limitation. These surfactants can be used alone, or in a combination of a few kinds.

It is preferable that the content of the surfactant is in a range of 0.001 to 5.0 wt. % based on the whole dental glass ionomer cement composition for luting.

Further, when the dental glass ionomer cement composition for luting of the present invention includes a paste form, a thickener can be contained to such a range that various properties are not influenced, for the purpose of improving paste property.

The dental glass ionomer cement composition for luting of the present invention can be use any of an inorganic ionic thickener and an organic thickener.

Specific examples of an inorganic thickener include fumed silica, calcium carbonate, calcium silicate, magnesium silicate, and a clay mineral such as saponite, montmorillonite, beidellite, vermiculite, sauconite, stevensite, hectorite, smectite, nekutaito and sepiolite. Specific examples of an organic thickener include methyl cellulose, hydroxyethyl cellulose, hydroxymethyl cellulose, hydroxypropyl cellulose, carboxymethyl cellulose, sodium carboxymethyl cellulose, calcium carboxymethyl cellulose, carboxypolymethylene, sodium alginate, propylene glycol alginate ester, sodium polyacrylate, starch, starch sodium glycolate, starch phosphate ester, polyvinyl pyrrolidone, carboxyvinyl polymer, khaya gum, arabic gum, karaya gum, guar gum. These thickeners may be used alone or as a mixture of two or more thereof.

It is preferable that the content of the thickener in the paste is in a range of 0.001 to 10.0 wt. %.

A non-acid reactive powder can be contained in the dental glass ionomer cement composition for luting of the present invention to such a range that various properties are not influenced, for the purpose of adjusting operability a mechanical characteristic or a setting characteristic.

As the non-acid reactive powder used in the dental glass ionomer cement composition for luting of the present invention, any non-acid reactive powder as long as the non-acid reactive powder does not contain element which may form chelate-bond with an acid group of the polymer of an acid group-containing polymerizable monomer can be used without any limitation. Examples of the non-acid reactive powder include known dental fillers such as an inorganic filler, an organic filler and an organic-inorganic complex filler, and these can be used alone or in a combination of a few of them. Among them, it is especially preferable that an inorganic filler is used. In addition, a shape of these non-acid reactive powder is not particularly limited, but arbitral particle shapes such as spherical, needle-like, plate-like, ground-like, and scaly-shapes and aggregate thereof may be used but not limited thereto. An average particle diameter of the non-acid reactive powder is not particular limited, but is preferably within a range of 0.001 to 30 μm.

Specific examples of the inorganic filler include quartz, amorphous silica, ultrafine silica, various glasses which does not contain element which may form chelate-bond with an acid group or alkaline metal salt of an acid group (including a glass by melting method, a glass produced by a vapor phase reaction, synthetic glass by sol-gel method and the like), silicon nitride, silicon carbide, boron carbide and the like, but is not limited thereto.

It is preferable that the content of the non-acid reactive powder is in a range of 0.001 to 40 wt. % based on the whole dental glass ionomer cement composition for luting.

The dental glass ionomer cement composition for luting of the present invention is provided in various forms such as powder material/liquid material, paste/liquid material, and paste/paste. In addition, it is preferable that the component (a) acid reactive glass powder and the component (b) polymer of an acid group-containing polymerizable monomer, or the component (a) acid reactive glass powder and the component (c) chelating agent are not coexist with in the presence of the component (d) water from the viewpoint of preservation stability.

Specific examples of the form of the powder material/liquid material include a combination of a powder material containing the component (a) acid reactive glass powder and a liquid material containing the component (b) polymer of an acid group-containing polymerizable monomer, the component (c) chelating agent and the component (d) water, a combination of a powder material containing the component (a) acid reactive glass powder and the component (b) polymer of an acid group-containing polymerizable monomer and a liquid material containing the component (c) chelating agent and the component (d) water, a combination of a powder material containing the component (a) acid reactive glass powder and the component (b) polymer of an acid group-containing polymerizable monomer and a liquid material containing the component (b) polymer of an acid group-containing polymerizable monomer, the component (c) chelating agent and the component (d) water, a combination of a powder material containing the component (a) acid reactive glass powder and the component (c) chelating agent and a liquid material containing the component (b) polymer of an acid group-containing polymerizable monomer and the component (d) water, a combination of a powder material containing the component (a) acid reactive glass powder and the component (c) chelating agent and a liquid material containing the component (b) polymer of an acid group-containing polymerizable monomer, the component (c) chelating agent and the component (d) water, a combination of a powder material containing the component (a) acid reactive glass powder, the component (b) polymer of an acid group-containing polymerizable monomer and the component (c) chelating agent and a liquid material containing the component (d) water, a combination of a powder material containing the component (a) acid reactive glass powder, the component (b) polymer of an acid group-containing polymerizable monomer and the component (c) chelating agent and a liquid material containing the component (b) polymer of an acid group-containing polymerizable monomer and the component (d) water, a combination of a powder material containing the component (a) acid reactive glass powder, the component (b) polymer of an acid group-containing polymerizable monomer and the component (c) chelating agent and a liquid material containing the component (c) chelating agent and the component (d) water, and a combination of a powder material containing the component (a) acid reactive glass powder, the component (b) polymer of an acid group-containing polymerizable monomer and the component (c) chelating agent and a liquid material containing the component (b) polymer of an acid group-containing polymerizable monomer, the component (c) chelating agent and the component (d) water, but not limited thereto.

Specific examples of the form of the paste/liquid material include a combination of a paste containing the component (a) acid reactive glass powder and the component (d) water and a liquid material containing the component (b) polymer of an acid group-containing polymerizable monomer, the component (c) chelating agent and the component (d) water, but not limited thereto.

Specific examples of the form of the paste/paste include a combination of a first paste containing the component (a) acid reactive glass powder and the component (d) water and a second paste containing the component (b) polymer of an acid group-containing polymerizable monomer, the component (c) chelating agent and the component (d) water, but not limited thereto.

Furthermore, the dental glass ionomer cement composition for luting of the present invention may optionally contain other conventionally known additives such as preservatives, antimicrobial materials, and coloring pigments.

EXAMPLES

The present invention is described in more detail and specifically with reference to Examples. However, the present invention is not limited to Examples.

(Details of the Component Used for Preparation of Dental Glass Ionomer Cement Composition for Luting)

The components (a) to (d) used for preparation of the dental glass ionomer cement composition for luting in Examples and Comparative Examples shown in Table 1.

TABLE 1

Component used for preparation of Examples and Comparative Examples

| | Raw materials | Abbreviation | | Polydispersity |
|---|---|---|---|---|
| | | | Average particle diameter (pm) | |
| Component (a) | Fluoroaluminosilicate glass 1 | FASG1 | 3.4 | |
| | Fluoroaluminosilicate glass 2 | FASG2 | 4.5 | |
| | Fluoroaluminosilicate glass 3 | FASG3 | 5.0 | |
| | Fluoroaluminosilicate glass 4 | FASG4 | 5.3 | |
| | Fluoroaluminosilicate glass 5 | FASG5 | 6.5 | |
| | Fluoroaluminosilicate glass 6 | FASG6 | 7.0 | |
| | Fluoroaluminosilicate glass 7 | FASG7 | 8.4 | |
| | | | Weight average molecular weight | |
| Component (b) | Copolymer of acrylic acid-tricarboxylic acid 1 | AA-TCA1 | 23000 | 1.64 |
| | Copolymer of acrylic acid-tricarboxylic acid 2 | AA-TCA2 | 30000 | 1.77 |
| | Copolymer of acrylic acid-tricarboxylic acid 3 | AA-TCA3 | 51000 | 2.53 |
| | Copolymer of acrylic acid-tricarboxylic acid 4 | AA-TCA4 | 70000 | 3.16 |
| | Copolymer of acrylic acid-tricarboxylic acid 5 | AA-TCA5 | 79000 | 3.07 |
| | Copolymer of acrylic acid-tricarboxylic acid 6 | AA-TCA6 | 100000 | 2.81 |
| | Copolymer of acrylic acid-tricarboxylic acid 7 | AA-TCA7 | 118000 | 2.78 |
| | Polyacrylic acid 1 | AA1 | 67000 | 1.77 |
| | Polyacrylic acid 2 | AA2 | 69000 | 2.56 |
| Component (c) | Tartaric acid | TA | | |
| | Maleic acid | MA | | |
| Component (d) | Ion-exchanged water | IEW | | |

The preparing method of the fluoroaluminosilicate glasses is as follows. (Preparing method of Fluoroaluminosilicate glass 1) Various raw material: silicon dioxide, aluminum oxide, sodium fluoride and strontium carbonate (glass composition: 23.8 wt. % of $SiO_2$, 16.2 wt. % of $Al_2O_3$, 35.6 wt. % of SrO, 2.3% wt. % of $Na_2O$ and 11.6 wt. % of F) were mixed and the mixed material was molten at 1400° C. in a melting furnace. The melt was taken out from the melting furnace and was quenched in water to prepare a glass. The resulting glass was pulverized to obtain acid reactive glass powder. The acid reactive glass powder was measured for an average particle diameter by a laser diffraction type grain size measuring apparatus (Microtrac MT3300EXII: NIK-KISO Co., Ltd.). The result was 3.4 μm.

(Preparing Methods of Fluoroaluminosilicate Glasses 2 to 7)

Fluoroaluminosilicate glasses 2 to 7 were prepared by the same method as in the Fluoroaluminosilicate glass 1 except that the average particle diameters were adjusted by pulverizing as shown in Table 1.

(Preparing Method of Copolymer of Acrylic Acid-Tricarboxylic Acid 1)

Both 70 parts by weight of acrylic acid and 30 parts by weight of 3-butene-1,2,3-tricarboxylic acid were added to the mixture of 150 mL of water and 150 parts by weight of methanol and ammonium persulfate was further added as a catalyst in a ratio of 2% based on a weight of the monomer. The mixture was heated to 60 to 70° C. to progress polymerization reaction for 4 hours under stirring. After the end of the reaction, the resulting solution was dried to obtain a polymer of an acid group-containing polymerizable monomer (Copolymer of acrylic acid-tricarboxylic acid 1). The polymer of an acid group-containing polymerizable monomer was measured for a weight average molecular weight and a polydispersity by a gel permeation chromatography (GCP-900: JASCO Corporation). The result was the weight average molecular weight of 23000 and the polydispersity of 1.64.

(Preparing Methods of Copolymers of Acrylic Acid-Tricarboxylic Acid 2 to 7)

Copolymers of acrylic acid-tricarboxylic acid 2 to 7 were prepared by the same method as in the Copolymer of acrylic acid-tricarboxylic acid 1 except that the weight average molecular weight and polydispersity were adjusted as shown in Table 1 by changing the reaction condition.

(Preparing Methods of the Polyacrylic Acids 1 and 2)

Polyacrylic acids 1 and 2 were prepared by the same method as in the Copolymer of acrylic acid-tricarboxylic acid 1 except that only acrylic acid is used as a monomer and the weight average molecular weight and polydispersity were adjusted as shown in Table 1 by changing the reaction condition.

(Preparation of Powder Material and Liquid Material)

Powder materials of P1 to P7 were prepared as shown in Table 2. In addition, Liquid materials L1 to 18 were prepared by mixing each components in a ratio shown in Table 3.

TABLE 2

| | | Composition of Powder Material | | | | | | |
|---|---|---|---|---|---|---|---|---|
| | | P1 | P2 | P3 | P4 | P5 | P6 | P7 |
| Com-<br>ponent<br>(a) | FASG1 | 100 | — | — | — | — | — | — |
| | FASG2 | — | 100 | — | — | — | — | — |
| | FASG3 | — | — | 100 | — | — | — | — |
| | FASG4 | — | — | — | 100 | — | — | — |
| | FASG5 | — | — | — | — | 100 | — | — |
| | FASG6 | — | — | — | — | — | 100 | — |
| | FASG7 | — | — | — | — | — | — | 100 |
| Total | | 100 | 100 | 100 | 100 | 100 | 100 | 100 |

TABLE 3

| | | Composition of Liquid Material | | | | | | | | | | | | | | | | | |
|---|---|---|---|---|---|---|---|---|---|---|---|---|---|---|---|---|---|---|
| | | L1 | L2 | L3 | L4 | L5 | L6 | L7 | L8 | L9 | L10 | L11 | L12 | L13 | L14 | L15 | L16 | L17 | L18 |
| Component<br>(b) | AA-TCA1 | 40 | — | — | — | — | — | — | — | — | — | — | — | — | — | — | — | — | — |
| | AA-TCA2 | — | 40 | — | — | — | — | — | — | — | — | — | — | — | — | — | 20 | 40 | — |
| | AA-TCA3 | — | — | 40 | — | — | — | — | — | — | — | — | — | — | — | — | — | — | — |
| | AA-TCA4 | — | — | — | 40 | — | — | — | — | — | 40 | 40 | — | 40 | 30 | 30 | — | — | — |
| | AA-TCA5 | — | — | — | — | 40 | — | — | — | — | — | — | — | — | — | — | — | — | — |
| | AA-TCA6 | — | — | — | — | — | 40 | — | — | — | — | — | 45 | — | — | — | — | — | 51 |
| | AA-TCA7 | — | — | — | — | — | — | 40 | — | — | — | — | — | — | — | — | — | — | — |
| | AA1 | — | — | — | — | — | — | — | 40 | — | — | — | — | — | — | — | — | — | — |
| | AA2 | — | — | — | — | — | — | — | — | 40 | — | — | — | — | — | — | — | — | — |
| Component<br>(c) | TA | 10 | 10 | 10 | 10 | 10 | 10 | 10 | 10 | 10 | — | 3 | 3 | 6 | 24 | 30 | 20 | 20 | 1 |
| | MA | — | — | — | — | — | — | — | — | — | 10 | — | — | — | — | — | — | — | — |
| Component<br>(d) | IEW | 50 | 50 | 50 | 50 | 50 | 50 | 50 | 50 | 50 | 50 | 57 | 52 | 54 | 46 | 40 | 60 | 40 | 48 |
| Total | | 100 | 100 | 100 | 100 | 100 | 100 | 100 | 100 | 100 | 100 | 100 | 100 | 100 | 100 | 100 | 100 | 100 | 100 |

The dental glass ionomer cement compositions for luting (Examples 1 to 20 and Comparative Examples 1 to 6) prepared by kneading the combination of these powder material and liquid material at the powder/liquid ratio shown in Tables 4 to 10 were evaluated. The evaluation methods are as follows. In addition, all the evaluations were carried out under the environmental of the room temperature of 23±1° C. and humidity of 50±10%.

(Plastic Flow Distance)

The kneaded material of 0.3 g was placed in a horizontal and smooth glass plane such that the diameter was within 10 mm and thereafter the glass plane was rotated to vertical to leave to stand until the kneaded material is set. After setting, a distance in which the kneaded material dripped and flowed by their own weights (a distance from the position of the lowermost end of the kneaded material before the plastic flow to the position of the lowermost end of the kneaded material after setting) was measured by 0.25 mm unit.

(Removal Possible Time of Excess Cement)

The kneaded material of 0.3 g was clamped between bottom surfaces of two rectangular resin blocks (12 mm of length×16 mm of width×10 mm of height) to strongly pressed by the two resin blocks to protrude the kneaded material from the clearance. Thereafter, it was placed into a thermostatic chamber of 37° C.—70% after 1 minute and 30 seconds from the start of kneading, and the protruded kneaded material was touched by a metal instrument every 15 seconds. The time from the placing into the thermostatic chamber to the timing where the protruded kneaded material can be removed in one lump.

(Drip of Excess Cement (Small Amount))

The kneaded material of 0.3 g of the dental glass ionomer cement composition for luting shown in each Examples and Comparative Examples was applied on an inner surface of a resin crown (mandibular first molar) and was pressure contacted with an abutment tooth model immediately thereafter. The state of the excess cement overflowed from the clearance between the crown and the abutment tooth model was observed.

The rating criteria are as follows.

A: No excess cement dripped and flowed.
B: Although excess cement dripped and flowed slightly it did not adversely affect removal characteristics after setting.
C: The removal after the setting became slightly complicated because of the dripped and flowed excess cement.
D: Excess cement dripped and flowed to the bottom surface of the abutment tooth model.

(Drip of Excess Cement (Large Amount))

The kneaded material of 0.6 g of the dental glass ionomer cement composition for luting shown in each Examples and Comparative Examples was applied on an inner surface of a resin crown (mandibular first molar) and was pressure contacted with an abutment tooth model immediately thereafter. The state of the excess cement overflowed from the clearance between the crown and the abutment tooth model was observed.

The rating criteria are as follows.

A: No excess cement dripped and flowed.
B: Although excess cement dripped and flowed slightly it did not adversely affect removal characteristics after setting.
C: The removal after the setting became slightly complicated because of the dripped and flowed excess cement.
D: Excess cement dripped and flowed to the bottom surface of the abutment tooth model.

(Kneadability)

Kneadability on kneading the powder material and the liquid material of the dental glass ionomer cement composition for luting shown in the Examples and Comparative Examples was evaluated.

The rating criteria are as follows.

A: There was little resistance feeling and it could be easily kneaded.
B: Although there was a little resistance feeling, it could be kneaded without a problem.

C: There was a large resistance feeling and it could be kneaded with difficulty.
D: There was a very large resistance feeling and it was substantially hard to knead.
(Viscosity of Kneaded Material)

The kneaded material of 0.3 g of the dental glass ionomer cement composition for luting shown in each Examples and Comparative Examples was applied on an inner surface of a resin crown (mandibular first molar) and was placed on an abutment tooth model immediately thereafter. After 1 minute from the start of kneading, the crown was added with 550 g of the load to pressure contact with the abutment tooth model.
The rating criteria are as follows.
A: The viscosity of the kneaded material was low enough, and the lift of the crown was not recognized at all.
B: Although the viscosity of the kneaded material was slightly low and the lift of the crown was not recognized by a visual observation, there was a room which can be slightly pushed by pressure contacting with a finger after loading the load.
C: The viscosity of the kneaded material was slightly high and the lift of the crown was slightly recognized by a visual observation.
D: The viscosity of the kneaded material was remarkably high and the lift of the crown was clearly recognized by a visual observation.
(Film Thickness)

By referring ISO 9917-1:2007 film thickness, a film thickness was measured by the following procedure. The kneaded material of the dental glass ionomer cement composition for luting shown in each Examples and Comparative Examples was clamped between two glass plates (circular shape) having 15 mm of in a diameter and then was applied with 150±2 N of the vertical stress after 1 minute from the start of the kneading. After maintaining until the kneaded material was set, a thickness of the kneaded material extended by force was measured as the film thickness. In addition, the dental glass ionomer cement for luting must have the film thickness of 25 μm by requirement of the ISO 9917-1:2007.
(Working Time)

A change of the film thickness with the elapsed time from a start of the kneading was confirmed by changing a timing of applying the vertical stress by 30 seconds after 1 minute from the start of the kneading in the evaluation method of the above film thickness test. The time from the start of the kneading to a timing where the film thickness of 25 μm was kept was measured as the working time. In addition, in the dental glass ionomer cement for luting, it is desirable to have the working time more than at least one minute from the start of the kneading.
(Compressive Strength)

A compressive strength was measured by the following procedures according to ISO 9917-1:2007. The kneaded material of the dental glass ionomer cement composition for luting shown in each Examples and Comparative Examples was filled in a stainless steel die (4 mm in diameter×6 mm in height) to leave to stand for 1 hour in a 37° C. and 100% thermohygrostat. The test specimen was taken out after 24 hours from the end of the kneading and an Instron universal tester (Instron 5567A manufactured by Instron Japan) was used to measure the compressive strength at a crosshead speed of 1 mm/min. In addition, the dental glass ionomer cement for luting must have the compressive strength of 50 MPa by requirement of the ISO 9917-1:2007.

Example 1 and Comparative Examples 1 to 6

Table 4 shows evaluation results of the dental glass ionomer cement compositions for luting shown in Example 1 and Comparative Examples 1 to 6.

In the Example 1, the excess cement did not drip and flow at all and preferable characteristics for the dental glass ionomer cement for luting with respect to the kneadability, the viscosity of the kneaded material, the working time, the film thickness and the compressive strength were exhibited.

The composition of the Comparative Example 1 was kneaded by using the Powder material P1 (consisting of the Fluoroaluminosilicate glass 1 having an average particle diameter of 3.4 μm) instead of the Powder material P4 (consisting of the Fluoroaluminosilicate glass 4 having an average particle diameter of 5.3 μm) in the Example 1.

In the Comparative Example 1, although the excess cement did not drip and flow at all and excellent compressive strength was exhibited, it was recognized that resistance feeling on the kneading was large, the viscosity of the kneaded material was remarkably high, the working time was short and the film thickness was thick.

The composition of the Comparative Example 2 was kneaded by using the Powder material P7 (consisting of the Fluoroaluminosilicate glass 7 having an average particle diameter of 8.4 μm) instead of the Powder material P4 (consisting of the Fluoroaluminosilicate glass 4 having an average particle diameter of 5.3 μm) in the Example 1 and the removal possible time of the excess cement exceeds 2 minutes in the Comparative Example 2.

In the Comparative Example 2, it was recognized that the excess cement dripped and flowed. In addition, although kneadability, the viscosity of the kneaded material and the compressive strength were excellent, it was recognized that the working time was short and the film thickness was thick.

The composition of the Comparative Example 3 was kneaded by using the Liquid material L1 (containing the Copolymer of acrylic acid-tricarboxylic acid 1 having the weight average molecular weight of 23000) instead of the Liquid material L4 (containing the Copolymer of acrylic acid-tricarboxylic acid 4 having the weight average molecular weight of 70000) in the Example 1 and the removal possible time of the excess cement exceeds 2 minutes in the Comparative Example 3.

In the Comparative Example 3, it was recognized that the excess cement dripped and flowed. With respect to other characteristics, preferable characteristics for the dental glass ionomer cement for luting were exhibited.

The composition of the Comparative Example 4 was kneaded by using the Liquid material L7 (containing the Copolymer of acrylic acid-tricarboxylic acid 7 having the weight average molecular weight of 118000) instead of the Liquid material L4 (containing the Copolymer of acrylic acid-tricarboxylic acid 4 having the weight average molecular weight of 70000) in the Example 1.

In the Comparative Example 4, although the excess cement did not drip and flow at all and the compressive strength was excellent, it was recognized that resistance feeling on the kneading was large, the viscosity of the kneaded material was remarkably high, the working time was short and the film thickness was thick.

The composition of the Comparative Example 5 was kneaded at a powder/liquid ratio of 1.0/1.0 in the Example 1 and the removal possible time of the excess cement exceeds 2 minutes in the Comparative Example 5.

In the Comparative Example 5, it was recognized that the excess cement dripped and flowed when the amount of the excess cement was large. With respect to other characteristics, preferable characteristics for the dental glass ionomer cement for luting were exhibited.

The composition of the Comparative Example 6 was kneaded at a powder/liquid ratio of 0.5/1.0 in the Example 1 and the removal possible time of the excess cement exceeds 2 minutes in the Comparative Example 6.

In the Comparative Example 6, it was recognized that the excess cement dripped and flowed remarkably and the compressive strength was low. With respect to other characteristics, preferable characteristics for the dental glass ionomer cement for luting were exhibited.

Examples 2 to 5

Table 5 shows evaluation results of the dental glass ionomer cement compositions for luting shown in Examples 2 to 5.

The composition of the Example 2 was kneaded by using the Powder material P2 (consisting of the Fluoroaluminosilicate glass 2 having an average particle diameter of 4.5 μm) instead of the Powder material P4 (consisting of the Fluoroaluminosilicate glass 4 having an average particle diameter of 5.3 μm) in the Example 1.

The composition of the Example 3 was kneaded by using the Powder material P3 (consisting of the Fluoroaluminosilicate glass 3 having an average particle diameter of 5.0 μm) instead of the Powder material P4 (consisting of the Fluoroaluminosilicate glass 4 having an average particle diameter of 5.3 μm) in the Example 1.

The composition of the Example 4 was kneaded by using the Powder material P5 (consisting of the Fluoroaluminosilicate glass 5 having an average particle diameter of 6.5 μm) instead of the Powder material P4 (consisting of the Fluoroaluminosilicate glass 4 having an average particle diameter of 5.3 μm) in the Example 1.

The composition of the Example 5 was kneaded by using the Powder material P6 (consisting of the Fluoroalumino-

TABLE 4

Combination and Evaluation result in Example 1 and Comparative Examples 1 to 6

| | | Example 1 | Comparative Example 1 | Comparative Example 2 | Comparative Example 3 | Comparative Example 4 | Comparative Example 5 | Comparative Example 6 |
|---|---|---|---|---|---|---|---|---|
| Powder material | | P4 | P1 | P7 | P4 | P4 | P4 | P4 |
| Liquid material | | L4 | L4 | L4 | L1 | L7 | L4 | L4 |
| Powder/Liquid ratio | | 2.0/1.0 | 2.0/1.0 | 2.0/1.0 | 2.0/1.0 | 2.0/1.0 | 1.0/1.0 | 0.5/1.0 |
| Component (a) | FASG1 | — | 66.7 | — | — | — | — | — |
| | FASG4 | 66.7 | — | — | 66.7 | 66.7 | 50.0 | 33.3 |
| | FASG7 | — | — | 66.7 | — | — | — | — |
| Component (b) | AA-TCA1 | — | — | — | 13.3 | — | — | — |
| | AA-TCA4 | 13.3 | 13.3 | 13.3 | — | — | 20.0 | 26.7 |
| | AA-TCA7 | — | — | — | — | 13.3 | — | — |
| Component (c) | TA | 3.3 | 3.3 | 3.3 | 3.3 | 3.3 | 5.0 | 6.7 |
| Component (d) | IEW | 16.7 | 16.7 | 16.7 | 16.7 | 16.7 | 25.0 | 33.3 |
| Total | | 100 | 100 | 100 | 100 | 100 | 100 | 100 |
| Plastic flow distance (mm) | | 0.00 | 0.00 | 2.00 | 1.50 | 0.00 | 1.25 | 5.25 |
| Removal possible time of surplus cement (mill:sec) | | 1:15 | 0:30 | 3:00 | 2:15 | 0:45 | 3:30 | 8:30 |
| Drip of surplus cement (small amount) | | A | A | C | C | A | B | D |
| Drip of surplus cement (large amount) | | A | A | D | D | A | D | D |
| Kneadability | | A | C | A | A | C | A | A |
| Viscosity of kneaded material | | A | D | A | A | D | A | A |
| Coating thickness (μm) | | 18 | 45 | 32 | 18 | 38 | 17 | 15 |
| Operation time (min:sec) | | 2:30 | Less than 1:00 | Less than 1:00 | 3:30 | Less than 1:00 | 5:00 | 12:00 |
| Compressive strength (Mpa) | | 175 | 181 | 129 | 145 | 203 | 72 | 34 | silicate glass 6 having an average particle diameter of 7.0 μm) instead of the Powder material P4 (consisting of the Fluoroaluminosilicate glass 4 having an average particle diameter of 5.3 μm) in the Example 1.

In the Examples 2 to 5, the excess cement hardly dripped and flowed and preferable characteristics for the dental glass ionomer cement for luting with respect to other characteristics were exhibited.

lar weight of 51000) instead of the Liquid material L4 (containing the Copolymer of acrylic acid-tricarboxylic acid 4 having the weight average molecular weight of 70000) in the Example 1.

The composition of the Example 8 was kneaded by using the Liquid material L5 (containing the Copolymer of acrylic acid-tricarboxylic acid 5 having the weight average molecular weight of 79000) instead of the Liquid material L4

TABLE 5

Combination and Evaluation result in Examples 2 to 5

|  |  | Example 2 | Example 3 | Example 4 | Example 5 |
|---|---|---|---|---|---|
|  | Powder material | P2 | P3 | P5 | P6 |
|  | Liquid material | L4 | L4 | L4 | L4 |
|  | Powder/Liquid ratio | 2.0/1.0 | 2.0/1.0 | 2.0/1.0 | 2.0/1.0 |
| Component (a) | FASG2 | 66.7 | — | — | — |
|  | FASG3 | — | 66.7 | — | — |
|  | FASG5 | — | — | 66.7 | — |
|  | FASG6 | — | — | — | 66.7 |
| Component (b) | AA-TCA4 | 13.3 | 13.3 | 13.3 | 13.3 |
| Component (c) | TA | 3.3 | 3.3 | 3.3 | 3.3 |
| Component (d) | IEW | 16.7 | 16.7 | 16.7 | 16.7 |
|  | Total | 100 | 100 | 100 | 100 |
| Plastic flow distance (mm) |  | 0.00 | 0.00 | 0.50 | 1.00 |
| Removal possible time of surplus cement (min:sec) |  | 0:45 | 1:00 | 1:30 | 1:45 |
| Drip of surplus cement (small amount) |  | A | A | A | A |
| Drip of surplus cement (large amount) |  | A | A | A | B |
| Kneadability |  | B | A | A | A |
| Viscosity of kneaded material |  | B | A | A | A |
| Coating thickness (μm) |  | 17 | 18 | 20 | 23 |
| Operation time (min:sec) |  | 1:30 | 2:00 | 3:00 | 3:30 |
| Compressive strength (Mpa) |  | 186 | 179 | 171 | 162 |

Examples 6 to 9

Table 6 shows evaluation results of the dental glass ionomer cement compositions for luting shown in Examples 6 to 9.

The composition of the Example 6 was kneaded by using the Liquid material L2 (containing the Copolymer of acrylic acid-tricarboxylic acid 2 having the weight average molecular weight of 30000) instead of the Liquid material L4 (containing the Copolymer of acrylic acid-tricarboxylic acid 4 having the weight average molecular weight of 70000) in the Example 1.

The composition of the Example 7 was kneaded by using the Liquid material L3 (containing the Copolymer of acrylic acid-tricarboxylic acid 3 having the weight average molecu- (containing the Copolymer of acrylic acid-tricarboxylic acid 4 having the weight average molecular weight of 70000) in the Example 1.

The composition of the Example 9 was kneaded by using the Liquid material L6 (containing the Copolymer of acrylic acid-tricarboxylic acid 6 having the weight average molecular weight of 100000) instead of the Liquid material L4 (containing the Copolymer of acrylic acid-tricarboxylic acid 4 having the weight average molecular weight of 70000) in the Example 1.

In the Examples 6 to 9, the excess cement hardly dripped and flowed and preferable characteristics for the dental glass ionomer cement for luting with respect to other characteristics were exhibited.

TABLE 6

Combination and Evaluation result in Examples 6 tp 9

|  |  | Example 6 | Example 7 | Example 8 | Example 9 |
|---|---|---|---|---|---|
|  | Powder material | P4 | P4 | P4 | P4 |
|  | Liquid material | L2 | L3 | L5 | L6 |
|  | Powder/Liquid ratio | 2.0/1.0 | 2.0/1.0 | 2.0/1.0 | 2.0/1.0 |
| Component (a) | FASG4 | 66.7 | 66.7 | 66.7 | 66.7 |
| Component (b) | AA-TCA2 | 13.3 | — | — | — |
|  | AA-TCA3 | — | 13.3 | — | — |
|  | AA-TCA5 | — | — | 13.3 | — |
|  | AA-TCA6 | — | — | — | 13.3 |
| Component (c) | TA | 3.3 | 3.3 | 3.3 | 3.3 |
| Component (d) | IEW | 16.7 | 16.7 | 16.7 | 16.7 |
|  | Total | 100 | 100 | 100 | 100 |
| Plastic flow distance (mm) |  | 0.75 | 0.00 | 0.00 | 0.00 |

TABLE 6-continued

Combination and Evaluation result in Examples 6 tp 9

|  | Example 6 | Example 7 | Example 8 | Example 9 |
|---|---|---|---|---|
| Removal possible time of surplus cement (min:sec) | 1:45 | 1:30 | 1:00 | 1:00 |
| Drip of surplus cement (small amount) | A | A | A | A |
| Drip of surplus cement (large amount) | B | A | A | A |
| Kneadability | A | A | A | B |
| Viscosity of kneaded material | A | A | A | B |
| Coating thickness (μm) | 18 | 18 | 20 | 22 |
| Operation time (min:sec) | 3:00 | 2:30 | 2:00 | 1:30 |
| Compressive strength (Mpa) | 155 | 168 | 183 | 194 |

Example 10

Table 7 shows evaluation results of the dental glass ionomer cement composition for luting shown in Example 10.

The composition of the Example 10 was kneaded by using the Liquid material L10 (containing maleic acid) instead of the Liquid material L4 (containing tartaric acid) in the Example 1.

In the Example 10, the excess cement did not drip and flow at all and preferable characteristics for the dental glass ionomer cement for luting with respect to other characteristics were exhibited.

TABLE 7

Combination and Evaluation result in Example 10

|  |  | Example 10 |
|---|---|---|
| Powder material |  | P4 |
| Liquid material |  | L10 |
| Powder/Liquid ratio |  | 2.0/1.0 |
| Component (a) | FASG4 | 66.7 |
| Component (b) | AA-TCA4 | 13.3 |
| Component (c) | MA | 3.3 |
| Component (d) | IEW | 16.7 |
| Total |  | 100 |
| Plastic flow distance (mm) |  | 0.00 |
| Removal possible time of surplus cement (min:sec) |  | 1:45 |
| Drip of surplus cement (small amount) |  | A |
| Drip of surplus cement (large amount) |  | A |
| Kneadability |  | A |
| Viscosity of kneaded material |  | A |
| Coating thickness (μm) |  | 18 |
| Operation time (min:sec) |  | 3:00 |
| Compressive strength (Mpa) |  | 184 |

Examples 11 to 14

Table 8 shows evaluation results of the dental glass ionomer cement compositions for luting shown in Examples 11 to 14.

The composition of the Example 11 was kneaded by using the Liquid material L12 (containing 45.0 wt. % of the Copolymer of acrylic acid-tricarboxylic acid 6, 3.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) at a powder/liquid ratio of 0.5/1.0 in the Example 2.

The composition of the Example 12 was kneaded at a powder/liquid ratio of 1.0/1.0 in the Example 11.

The composition of the Example 13 was kneaded by using the Liquid material L17 (containing 40.0 wt. % of the Copolymer of acrylic acid-tricarboxylic acid 2, 20.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) at a powder/liquid ratio of 3.0/1.0 in the Example 5.

The composition of the Example 14 was kneaded by using the Liquid material L16 (containing 20.0 wt. % of the Copolymer of acrylic acid-tricarboxylic acid 2, 20.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) at a powder/liquid ratio of 3.0/1.0 in the Example 5.

In the Examples 11 to 14, the excess cement hardly dripped and flowed and preferable characteristics for the dental glass ionomer cement for luting with respect to other characteristics were exhibited.

TABLE 8

Combination and Evaluation result in Examples 11 to 14

|  |  | Example 11 | Example 12 | Example 13 | Example 14 |
|---|---|---|---|---|---|
| Powder material |  | P2 | P2 | P6 | P6 |
| Liquid material |  | L12 | L12 | L17 | L16 |
| Powder/Liquid ratio |  | 0.5/1.0 | 1.0/1.0 | 3.0/1.0 | 3.0/1.0 |
| Component (a) | FASG2 | 33.3 | 50.0 | — | — |
|  | FASG6 | — | — | 75.0 | 75.0 |
| Component (b) | AA-TCA2 | — | — | 10.0 | 5.0 |
|  | AA-TCA6 | 30.0 | 22.5 | — | — |

TABLE 8-continued

Combination and Evaluation result in Examples 11 to 14

|  |  | Example 11 | Example 12 | Example 13 | Example 14 |
|---|---|---|---|---|---|
| Component (c) | TA | 2.0 | 1.5 | 5.0 | 5.0 |
| Component (d) | IEW | 34.7 | 26.0 | 10.0 | 15.0 |
| Total | | 100 | 100 | 100 | 100 |
| Plastic flow distance (mm) | | 2.00 | 1.00 | 0.00 | 0.00 |
| Removal possible time of surplus cement (mm:sec) | | 2:00 | 1:30 | 1:15 | 1:45 |
| Drip of surplus cement (small amount) | | B | A | A | A |
| Drip of surplus cement (large amount) | | B | B | A | A |
| Kneadability | | A | A | B | B |
| Viscosity of kneaded material | | A | A | B | B |
| Coating thickness (μm) | | 15 | 17 | 24 | 23 |
| Operation time (min:sec) | | 5:00 | 3:00 | 1:30 | 2:00 |
| Compressive strength (Mpa) | | 51 | 101 | 179 | 121 |

Examples 15 and 16

Table 9 shows evaluation results of the dental glass ionomer cement compositions for luting shown in Examples 15 to 16.

The composition of the Example 15 was kneaded by using the Liquid material L18 (containing the Polyacrylic acid 1 having a polydispersity of 0.77) instead of the Liquid material L4 (containing the Copolymer of acrylic acid-tricarboxylic acid 4 having a polydispersity of 3.16) in the Example 1.

The composition of the Example 16 was kneaded by using the Liquid material L19 (containing the Polyacrylic acid 2 having a polydispersity of 2.56) instead of the Liquid material L4 (containing the Copolymer of acrylic acid-tricarboxylic acid 4 having a polydispersity of 3.16) in the Example 1.

In the Examples 15 and 16, the excess cement hardly dripped and flowed and preferable characteristics for the dental glass ionomer cement for luting with respect to other characteristics were exhibited.

TABLE 9

Combination and Evaluation result in Examples 15 to 16

|  |  | Example 15 | Example 16 |
|---|---|---|---|
| Powder material | | P4 | P4 |
| Liquid material | | L8 | L9 |
| Powder/Liquid ratio | | 2.0/1.0 | 2.0/1.0 |
| Component (a) | FASG4 | 66.7 | 66.7 |
| Component (b) | AA1 | 13.3 | — |
|  | AA2 | — | 13.3 |
| Component (c) | TA | 3.3 | 3.3 |
| Component (d) | IEW | 16.7 | 16.7 |
| Total | | 100 | 100 |
| Plastic flow distance (mm) | | 1.00 | 0.50 |
| Removal possible time of surplus cement (min:sec) | | 1:45 | 1:30 |
| Drip of surplus cement (small amount) | | A | A |
| Drip of surplus cement (large amount) | | B | A |
| Kneadability | | A | A |
| Viscosity of kneaded material | | A | A |
| Coating thickness (μm) | | 17 | 18 |
| Operation time (min:sec) | | 3:00 | 2:30 |
| Compressive strength (Mpa) | | 172 | 178 |

Examples 17 to 20

Table 10 shows evaluation results of the dental glass ionomer cement compositions for luting shown in Examples 17 to 20.

The composition of the Example 17 was kneaded by using the Liquid material L11 (containing 40.0 wt. % of the Copolymer of acrylic acid-tricarboxylic acid 4, 3.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) in the Example 1.

The composition of the Example 18 was kneaded by using the Liquid material L13 (containing 40.0 wt. % of the Copolymer of acrylic acid-tricarboxylic acid 4, 6.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) in the Example 1.

The composition of the Example 19 was kneaded by using the Liquid material L14 (containing 30.0 wt. % of the Copolymer of acrylic acid-tricarboxylic acid 4, 24.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) in the Example 1.

The composition of the Example 20 was kneaded by using the Liquid material L15 (containing 30.0 wt. % of the Copolymer of acrylic acid-tricarboxylic acid 4, 30.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) in the Example 1.

In the Examples 17 to 20, the excess cement hardly dripped and flowed and preferable characteristics for the dental glass ionomer cement for luting with respect to other characteristics were exhibited.

TABLE 10

Combination and Evaluation result in Examples 17 to 20

|  |  | Example 17 | Example 18 | Example 19 | Example 20 |
|---|---|---|---|---|---|
|  | Powder material | P4 | P4 | P4 | P4 |
|  | Liquid material | L11 | L13 | L14 | L15 |
|  | Powder/Liquid ratio | 2.0/1.0 | 2.0/1.0 | 2.0/1.0 | 2.0/1.0 |
| Component (a) | FASG4 | 66.7 | 66.7 | 66.7 | 66.7 |
| Component (b) | AA-TCA4 | 13.3 | 13.3 | 10.0 | 10.0 |
| Component (c) | TA | 1.0 | 2.0 | 8.0 | 10.0 |
| Component (d) | IEW | 19.0 | 18.0 | 15.3 | 13.3 |
|  | Total | 100 | 100 | 100 | 100 |
|  | Plastic flow distance (mm) | 0.00 | 0.00 | 0.75 | 0.50 |
|  | Removal possible time of surplus cement (mm:sec) | 0:45 | 1:00 | 1:30 | 1:30 |
|  | Drip of surplus cement (small amount) | A | A | A | A |
|  | Drip of surplus cement (large amount) | A | A | A | A |
|  | Kneadability | B | A | A | A |
|  | Viscosity of kneaded material | B | A | A | A |
|  | Coating thickness (µm) | 18 | 18 | 17 | 17 |
|  | Operation time (min:sec) | 1:00 | 1:30 | 3:00 | 2:30 |
|  | Compressive strength (Mpa) | 167 | 173 | 133 | 139 |

Examples 21 to 22

Table 11 shows evaluation results of the dental glass ionomer cement compositions for luting shown in Examples 21 to 22.

The composition of the Example 21 was kneaded at a powder/liquid ratio of 4.0/1.0 in the Example 14.

The composition of the Example 22 was kneaded by using the Liquid material L18 (containing 51.0 wt. % of the Copolymer of acrylic acid-tricarboxylic acid 6, 1.0 wt. % of tartaric acid and a residual part of water) instead of the Liquid material L4 (containing 40.0 wt. % of the Copolymer of acrylic acid-tricarboxylic acid 4, 10.0 wt. % of tartaric acid and a residual part of water) in the Example 2.

In the Examples 21 and 22, the excess cement hardly dripped and flowed and preferable characteristics for the dental glass ionomer cement for luting with respect to other characteristics were exhibited.

TABLE 11

Combination and Evaluation result in Examples 21 to 22

|  |  | Example 21 | Example 22 |
|---|---|---|---|
|  | Powder material | P6 | P2 |
|  | Liquid material | L16 | L18 |
|  | Powder/Liquid ratio | 4.0/1.0 | 1.0/3.0 |
| Component (a) | FASG2 |  | 25.0 |
|  | FASG6 | 80.0 |  |
| Component (b) | AA-TCA2 | 4.0 |  |
|  | AA-TCA6 |  | 38.2 |
|  | AA-TCA7 |  |  |
| Component (c) | TA | 4.0 | 0.8 |
| Component (d) | IEW | 12.0 | 36.0 |
|  | Total | 100 | 100 |
|  | Plastic flow distance (mm) | 0.00 | 2.00 |
|  | Removal possible time of surplus cement (min:sec) | 1:30 | 2:00 |
|  | Drip of surplus cement (small amount) | A | B |
|  | Drip of surplus cement (large amount) | A | B |
|  | Kneadability | B | A |
|  | Viscosity of kneaded material | B | A |
|  | Coating thickness (µm) | 2:00 | 3:30 |
|  | Operation time (min:sec) | 25 | 15 |
|  | Compressive strength (Mpa) | 115 | 62 |

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

The present invention provides a glass ionomer cement having excellent removality of the excess cement after setting because of having shape retaining property where a kneaded material does not drip and flow by their own weights, few risk of water sensitivity and excellent operability at the bonding such that excess cement can be removed easily after an application in an oral cavity in an early timing in spite of exhibiting a thin film thickness at the bonding.

What is claimed is:

1. A dental glass ionomer cement composition for luting comprising at least;

a component (a) acid reactive glass powder having an average particle diameter within a range of 4.5 to 7.0 µm, a component (b) polymer of an acid group-containing polymerizable monomer having a weight average molecular weight within a range of 30000 to 100000, a component (c) chelating agent and a component (d) water, wherein a plastic flow distance of a kneaded material before setting is 2 mm or less, and a removal possible time of an excess cement is 2 minutes or less.

2. The dental glass ionomer cement composition for luting according to claim 1, wherein the plastic flow distance of the kneaded material before setting is 1 mm or less, and the removal possible time of the excess cement is 1 minute and 30 seconds or less.

3. The dental glass ionomer cement composition for luting according to claim 1, comprising;
- 30.0 to 75.0 wt. % of the component (a) acid reactive glass powder having an average particle diameter within a range of 4.5 to 7.0 µm,
- 5.0 to 30.0 wt. % of the component (b) polymer of an acid group-containing polymerizable monomer having a weight average molecular weight within a range of 30000 to 100000,
- 1.0 to 10.0 wt. % of the component (c) chelating agent, and
- 10.0 to 35.0 wt. % of the component (d) water.

4. The dental glass ionomer cement composition for luting according to claim 1, wherein
the average particle diameter of the component (a) acid reactive glass powder is within a range of 5.0 to 6.5 µm.

5. The dental glass ionomer cement composition for luting according to claim 1, wherein
the component (b) polymer of an acid group-containing polymerizable monomer is a polymer of an α-β unsaturated carboxylic acid.

6. The dental glass ionomer cement composition for luting according to claim 1, wherein
the weight average molecular weight of the component (b) polymer of an acid group-containing polymerizable monomer is within a range of 50000 to 80000.

7. The dental glass ionomer cement composition for luting according to claim 1, wherein
the component (c) chelating agent is tartaric acid.

8. The dental glass ionomer cement composition for luting according to claim 1, wherein
the component (b) polymer of an acid group-containing polymerizable monomer is a polymer of acrylic acid and 1-buten-1,2,4-tricarboxylic acid and/or a polymer of acrylic acid and 3-buten-1,2,3-tricarboxylic acid.

9. The dental glass ionomer cement composition for luting according to claim 2, comprising;
- 30.0 to 75.0 wt. % of the component (a) acid reactive glass powder having an average particle diameter within a range of 4.5 to 7.0 µm,
- 5.0 to 30.0 wt. % of the component (b) polymer of an acid group-containing polymerizable monomer having a weight average molecular weight within a range of 30000 to 100000,
- 1.0 to 10.0 wt. % of the component (c) chelating agent, and
- 10.0 to 35.0 wt. % of the component (d) water.

10. The dental glass ionomer cement composition for luting according to claim 9, wherein
the average particle diameter of the component (a) acid reactive glass powder is within a range of 5.0 to 6.5 µm.

11. The dental glass ionomer cement composition for luting according to claim 10, wherein
the component (b) polymer of an acid group-containing polymerizable monomer is a polymer of an α-β unsaturated carboxylic acid.

12. The dental glass ionomer cement composition for luting according to claim 11, wherein
the weight average molecular weight of the component (b) polymer of an acid group-containing polymerizable monomer is within a range of 50000 to 80000.

13. The dental glass ionomer cement composition for luting according to claim 12, wherein
the component (c) chelating agent is tartaric acid.

14. The dental glass ionomer cement composition for luting according to claim 13, wherein
the component (b) polymer of an acid group-containing polymerizable monomer is a polymer of acrylic acid and 1-buten-1,2,4-tricarboxylic acid and/or a polymer of acrylic acid and 3-buten-1,2,3-tricarboxylic acid.

\* \* \* \* \*